June 2, 1964 C. C. BRUNES Plant Pat. 2,407

STRAWBERRY PLANT

Filed Oct. 29, 1962

INVENTOR
CHARLES C. BRUNES
BY
Williamson & Palmatier
ATTORNEYS

United States Patent Office

Plant Pat. 2,407
Patented June 2, 1964

2,407
STRAWBERRY PLANT
Charles C. Brunes, Pequot Lakes, Minn.
Filed Oct. 29, 1962, Ser. No. 233,988
1 Claim. (Cl. Plt.—49)

My present invention relates to a new and distinct variety of everbearing strawberry plant, which originated as a seedling, grown and discovered in my cultivated strawberry fields at Pequot Lakes, Minnesota. I have asexually reproduced from the original mother plant discovered in my said fields, a very large number of distinctive plants of this new variety by transplating rooted runner plants thereof.

An object of my invention has been to produce a new variety of strawberry plant of the everbearing type having greater productivity and capable of greater continuity of fruit production throughout the entire growing season than is usual in most outstanding everbearing varieties.

A further object has been to produce such an improved everbearing strawberry plant which is extremely hardy, resistant to common insects and pests and to drought, capable of being grown in light, sandy and heavier soils and having an inherent sweetness and lack of acidity not present in most other known varieties.

For more than nine years I have carried out a careful program of selection of new plants, testing my selections against the finest everbearing strawberry plants available in the American market with a view to producing a new and distinct variety having the characteristics previously described, with uniformity of shape, attractive appearance, taste texture, sweetness of the berry, and the most desirable amount of runner-production.

During the past nine years my production and selective program has included the raising of such strawberries as the well known unpatented "Gem," the unpatented "Ogalalla," the Brunes "Marvel," an unpatented berry produced first many years ago by me, the plants of Plant Patent No. 1,183, "Brilliant," and the plants of my Plant Patent No. 1,989, "Honey Lump."

My new and distinct variety of strawberry plant has been discovered and produced as a result of said program and may be generally characterized by its greater hardiness, fruit productivity, multiplication capacity throughout the entire season, its uniformity of berry shape and its unusual sweetness and taste texture.

I have made careful observations of all of the strawberry plants grown on my fields to detect resistance to common insects and diseases such as "leaf roller," "leaf hopper," "yellows" and "leaf spot." My observations shows that the plants of my new and distinct variety are resistant to all of such named inserts and diseases to an extent equal or superior to the varieties heretofore mentioned herein.

As to the disease, leaf spot, which I understand is caused by bacteria and fungus, and leaf roller, which I understand is brought about through insects, more specifically a certain variety of worms, the leaves and plants of my new berry showed substantially better resistance than in the case of the "Gem" plants and "Brilliant" plants of my production planted in the same soil, side-by-side with my new improved plants.

My determinations were made by side-to-side comparison of my improved strawberry plant with "Gem" and "Brilliant" plants planted in the same soil and treated in the same manner.

The berries of all of the asexually produced plants of my new variety are unusual in that they are almost universally of symmetrical conical, tapered shape, rounded uniformly at the upper shoulders throughout the circumference of the berry and tapering to pointed extremities.

My new berry is further characterized by heavy crowns producing large crops of berries and by runners which quickly grow into plants, and as soon as they take root, many start bearing. The berries of said runners develop to the full size of the mother plant during the first season.

The central portion of the berry is substantially firm and solid throughout although of a delicate, as distinguished from a coarse, taste-texture. The berries in external aspect are glossy, with less conspicuous seeds, slightly indented in the peripheral surface. The color of the prime, fully ripened berries is intense, medium dark red, darker than the "Gem" and slightly lighter than the "Ogalalla."

The taste-texture is excellent, medium juicy and of greater sweetness than any other strawberry plants I have ever grown or sampled, including all the varieties heretofore mentioned, as well as the berries of my Plant Patent No. 1,989.

The calyx of the berries of my new variety is separated from the base of the berry and the tips thereof point downwardly towards the stem and are not attached to the berry, as is clearly shown in the accompanying drawing.

My new variety, in the vicinity of my strawberry fields at Pequot Lakes, Minnesota, starts blooming about May 15th for the June crop and continues throughout the entire growing season. The first berries in prime condition appear about June 15th and berries continue in prime condition and full size from main plants and rooted runners throughout the entire season until the first killing frost which usually, in my area, approximates October 10th.

In the accompanying drawings, several typical berries as well as blossoms are illustrated in color and also, a complete plant of my new distinctive variety, growing in the field with berries, leaves and blossoms thereon.

Figure 1:
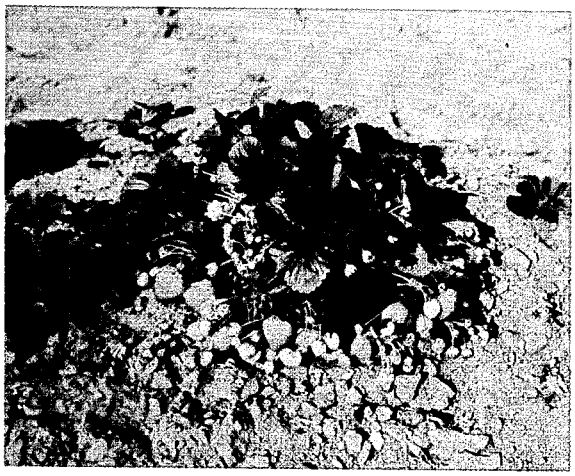
FIG. 1 is a perspective colored view of a typical plant of my new variety growing in the soil with berries in various stages of ripening thereon and with blossoms, and showing runner plants which have very recently rooted and leafed.

As a convenient summary and in instances with comparison of characteristics with other well known varieties, the following is a detailed description of my new variety of strawberry plant.

*Plant Characteristics*

Growth: Vigorous and hardy with many fruit stems and petioles, heavily leafed and rapid growth of new plants from runners.

Root size: Thick and relatively long, fast growing and clustered.

Crown size: Large and full; larger than the crowns of the plants of Plant Patent No. 993, Red Rich, and No. 1,183 as well as the "Gem"; about equal size to the crowns of Plant Patent No. 1,989 and the "Ogalalla" plant.

Leaf size and shape: Almost always trifoliate; larger than those of Patents No. 993 and 1,183; bright green in color but somewhat lighter green than the leaves of my Plant Patent No. 1,989 and the "Ogalalla" plant. Leaves characterized by uniform sawtooth serrations defining the periphery.

Petiole: Slightly more slender than those of the Brunes "Marvel" and of Plant Patents Nos. 1,183 and 993. Medium length and substantially shorter than its fruit stems, and having substantial pubescence.

Leaflets: Generally rounded periphery and generally cupped upwardly and almost as broad as they are long. Upper surface smooth and lower surface has medium pubescence.

Runners: Heavy stolons often as long as 11 to 13 inches, characterized by very rapid maturity, and when they are rooted, bear heavier than the plants of Patents 993, 1,183 and all other herein identified known varieties.

Flower stems: Relatively thick, generally green in color with no brown tinges; longer than most strawberry plants including those of Patents Nos. 993; 1,183 and the "Gem" plant.

Flowers: Blossoms quite perfect with petals defined by outwardly converging curved lines rather than arcuate lines, particularly characterized as shown in the drawings, by a number of unusually long stamens at the outer edges of the centers and with centers of deep yellow. Also characterized by the fact that the calyx is not closely adherent to the petals.

Sex: Bi-sexual.

Fruit stems: Sturdy and generally upright, many branch stems; slight pubescence. Longer than the fruit stems of the "Gem" plant and Plant Patents Nos. 993, and 1,183, and slightly longer than the fruit stems of the "Ogalalla" and my Plant Patent No. 1,989, said stems holding the berries well above the foliage of the leaves in exposure to the sun and to facilitate easy picking, in normally dry weather. (The illustrations of the actual plants were taken in comparatively wet weather where the berries are not shown above the foliage).

Soil: Plants grow well in rather poor sandy type soils as well as in richer and heavier soils.

Frost resistance: Hardy; excellent in typical Northern U.S. climate where humidity during the months of August through October averages over 50% and frost frequent after October 8th.

Resistance to rain and moisture: Excellent. As contrasted with "Gem," "Brilliant" and "Dunlap," after heavy rains and substantial periods of damp weather, the berries do not crack or split to the extent of said enumerated berries.

Drought resistance: Excellent. My new berry stands dry weather well, as proven through a number of dry spells in successive seasons when several other varieties, including "Dunlap" and "Gem" were wilting; my said variety withstood wilting. My conclusions and results are based on side-by-side comparisons of my new berry and the others enumerated, under the same climatic and soil conditions, after rather prolonged periods of drought.

*Fruit Characteristics*

Conditions: Prime, as described herein; prime and of substantially uniform size and shape during entire growing season, usually from the second or third weeks of June through the first week of October.

Size: Larger in volume than berries of Patents Nos. 993 and 1,989, and "Ogalalla," substantially equal to "Gem," averaging in normal seasons a maximum diameter of between 1¼ and 1⅜ inches.

Shape: Almost universally of symmetrical, tapered, conical shape, uniformly rounded at the upper shoulders thereof and tapering to pointed extremities; size and shape of ripened berries varying little during the entire growing season on runner plants as well as mother plants.

Surface aspects: Glossy and rather uniform surface throughout contour with only occasional protrusions or bumps. Surface color quite uniform throughout contour; intense medium dark red; color within range as illustrated in Dictionary of Color by Maerz and Paul, 2nd edition, published by McGraw-Hill Book Company, Inc., 1950, as illustrated on page 35, Plate 6, vertical column L varying between horizontal rows 5 and 8 inclusive; deeper red and less orange than "Gem"; slightly lighter red than "Ogalalla"; deeper red than Patent No. 1,183.

Flesh and interior: Texture medium; not as coarse as "Gem," "Ogalalla," or Patents Nos. 993 and 1,183; very firm with little if any void core; medium juicy; color of flesh adjacent periphery of berry only slightly lighter than surface color and as shown on page 35, Plate 6 of said Dictionary of Color by Maerz and Paul, within range in horizontal row 10 between vertical columns J to L inclusive; interior flesh further characterized almost universally by a relatively thin, narrow oval of white flesh, tapering longitudinally of the berry to a pointed lower extremity, and being less pronounced than in berries of Patents No. 993 and 1,183, and dissimilarly shaped; eating texture pleasing.

Seeds: Smaller and less conspicuous than in "Gem," "Ogalalla," and Patents Nos. 993, 1,183 and 1,989; slightly indented in periphery of berry.

Flavor: Very sweet; sweeter by far than "Gem," "Ogalalla," and the berries of Patents Nos. 993 and 1,183; somewhat sweeter than berries of Patent No. 1,989; absence of any tart or acidic taste.

Calyx: Medium size, sharply pointed sepals, unusual in that these sepals are freed from and do not extend against the lower shoulders of the berry but point downwardly towards the stem; scant pubescence; both surfaces of sepals light green color.

Uses and shipping qualities: Extremely good dessert quality; prefer eating without sugar; excellent for canning and freezing and will retain firmness and quality in shipping for approximately two days at temperatures approximating 70 degrees.

Figure 2:
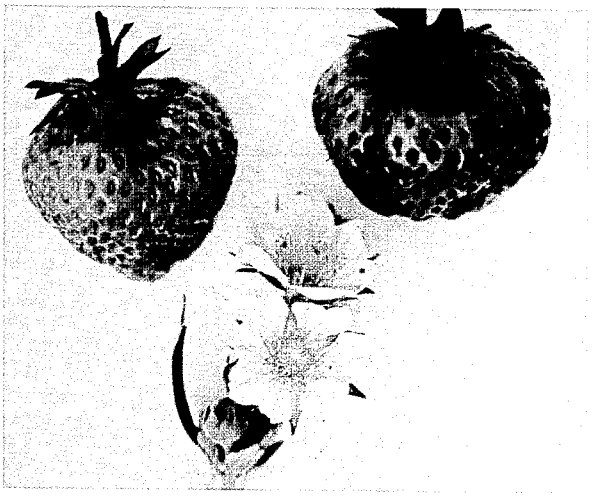
FIG. 2 is a perspective colored view showing two typical berries in prime condition, together with a pair of typical blossoms and the upper end of the blossom stems, with some leaflets thereon.
Figure 3:
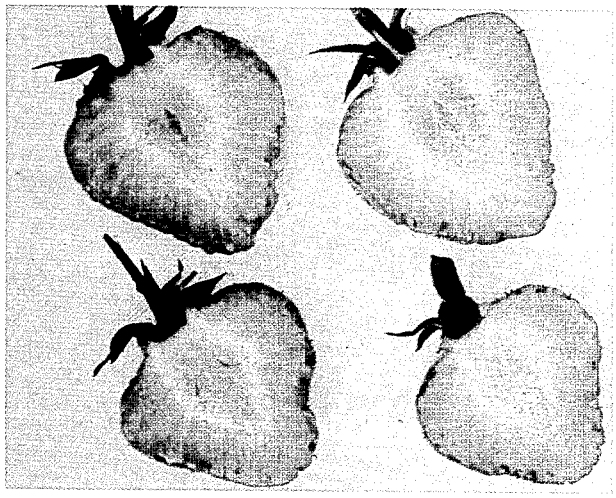
FIG. 3 is a perspective view of another pair of typical strawberries of my invention, which have been axially or stem-sliced to show the interior flesh.

None of the berries, as illustrated in FIG. 1, had advanced to full ripeness and the deeper coloring of the prime berries illustrated in FIGS. 2 and 3.

The strawberry described above and the plant producing the same may vary in slight details, depending upon weather conditions and soil conditions under which they are grown.

What I claim is:

A new and distinct variety of everbearing strawberry plant substantially as herein disclosed, characterized by a very sweet, non-acid flavor of the fruit, firmness of the flesh of the fruit throughout, having a medium-glossy and intense medium-dark red color within the range described herein, the fruit of said plant being almost universally of symmetrical tapered conical shape, uniformly rounded at the upper shoulders thereof and tapering to pointed extremities, said plant being further characterized by its prolific and rapid production of hearty runner plants, many of which bear a heavy crop of fruit the first season and are well adapted to grow and multiply prolifically in many types of soil under a variety of extreme weather conditions, the fruit having a calyx with sepals which extend downwardly from the base of the fruit toward the stem.

No references cited.